(12) United States Patent
Ma

(10) Patent No.: US 6,943,008 B1
(45) Date of Patent: Sep. 13, 2005

(54) BIOREACTOR FOR CELL CULTURE

(75) Inventor: Teng Ma, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 11 days.

(21) Appl. No.: 10/918,657

(22) Filed: Aug. 12, 2004

Related U.S. Application Data

(63) Continuation-in-part of application No. 10/645,350, filed on Aug. 21, 2003, now Pat. No. 6,875,605.

(60) Provisional application No. 60/405,040, filed on Aug. 21, 2002, provisional application No. 60/405,041, filed on Aug. 21, 2002, provisional application No. 60/494,907, filed on Aug. 13, 2003.

(51) Int. Cl.$^7$ .............................................. C12N 5/02
(52) U.S. Cl. ................................ 435/297.1; 435/399
(58) Field of Search ............................. 435/297.1, 399

(56) References Cited

OTHER PUBLICATIONS

Rainger et al., Journal of Immunological Methods, vol. 225 (2001), pp. 73-82.*
Pazzano et al.; "Comparison of Chondrogenis in Static and Perfused Bioreactor Culture;" Biotechnol. Prog vol. 16; No. 5; pp. 893-896; 2000.
Ingram et al.; "Three-Dimensional Growth Patterns of Various Human Tumor Cell Lines in Simulated Microgravity of A NASA Bioreactor;" In Vitro Cell. Dev. Biol.—Annual ; pp. 459-466; Jun. 1997.
Saini et al.; "Concentric Cylinder Bioreactor For Production of Tissue Engineered Cartilage: Effect of Seeding Density and Hydrodynamic Loading on Construct Development;" Biotechnol. Prog. 2003 vol. 19; (2003); pp. 510-521.
Cabrita et al.; "Hematopoietic stem cells: from the bone to the bioreactor;" Trends in Biotechnology; TIBTEC 45; 2003.
Bannu et al.; "Cytokine-Augumented Culture of Haematopoietic Progenitor Cells in a Novel Three-Dimensional Cell Growth Matrix;" Cytokine; vol. 13, No. 6; Mar. 21, 2000; pp. 349-358.
Blythe et al.; "Seroprevalence of antibodies to Sarcocystis neurona in horses residing in Oregon;" Journal of the American Veterinary Medical Association; vol. 210, No. 4, Feb. 15,. 1997; pp. 525-527.
Bagley et al., "Extended culture of miltipotent hematopoietic progenitors without cytokine augmentation in a novel three-dimensional device;" Experimental Hematoloty 27 (1999); pp. 496-504.
Obradovic et al.; "Gas Exchange is Essential for Bioreactor Cultivation of Tissue Engineered Cartilage;" Biotechnology and Bioengineering; vol. 63, No. 2, Apr. 20, 1999; pp. 197-205.

Hoerstrup, MD et al.; "New Pulsatile Bioreactor for in Vitro Formation of Tissue Engineered Heart Valves;" Tissue Engineering; vol. 6, No. 1, 2000; pp. 75-78.
Halberstadt et al.; "The In Vitro Growth of a Three-Dimensional Human Dermal Replacement Using a Single-Pass Perfusion System;" Biotechnology and Bioengineering; vol. 43, No. 4, 1994; pp. 740-746.
Vunjak et al., "Dynamic Cell Seeding of Polymer Scaffolds for Cartilage Tissue Engineering;" Biotechnol. Prog. 1998, vol. 14, No. 2; pp. 193-202.
Kim, MD et al.; "Dynamic Seeding and in Vitro Culture of Hepatocytes in a Flow Perfusion System;" Tissue Engineering; vol. 6, No. 1, 2000; pp. 39-44.
Ma et al.; "Development of an In Vitro Human Placenta Model by the Cuotivation of Human Trophoblasts in a Fiber-Based Bioreactor System;" Tissue Engineering; vol. 5, No. 2; (1999); pp. 91-101.
Freed et al.; "Cuotivation of Cell-Polymer Cartilage Implants in Bioreactors;" Journal of Cellular Biochemistry vol. 51; 1993; pp. 257-264.
Sittinger; "Artificial tissues in perfusion culture;" The International Journal of Artificial Organs; vol. 20, No. 1; 1997; pp. 57-62.
Niklason; "Functional Arteries Grown In Vitro;" Science; vol. 284; Apr. 16, 1999; pp. 489-493.
Nielsen; "Bioreactors For Hematopoietic Cell Culture;" Annu. Rev. Biomed. Eng.; 1999; pp. 129-152.
Li et al., "Human Cord Cell Hematopoiesis in Three Dimensional Nonwoven Firbous Matrices: In Vitro Simulation of the Marrow Microenvironment", Jounral of Hematotherapy & Stem Cell Research; vol. 10; 2001; pp. 355-368.
Collins et al.; "Characterization of Hematopoietic Cell Expansion, Oxygen Uptake, and Glycolysis in a Controlled, Stirred-Tank Bioreactor System;" Biotechnol. Prog. 1998 vol. 14; pp. 466-472.
Ma et al; "Oxygen Tension Influences Proliferation and Differentiation in a Tissue-Engineered Model of Pleacntal Trophoblast-Like Cells;" Tissue Engineering vol. 7; No. 5; 2001; pp. 496-506.

* cited by examiner

Primary Examiner—James Ketter
(74) Attorney, Agent, or Firm—Allen, Dyer, Doppelt, Milbrath & Gilchrist, P.A.

(57) ABSTRACT

A bioreactor for cell culture includes a chamber having three channels therethrough for conducting fluids, the three channels including an upper channel, a middle channel, and a lower channel, each the channel having an inlet and an outlet approximately opposite along the channel from the inlet. First and second cell support scaffolds are positioned within the chamber, each scaffold comprising at least one three-dimensional porous matrix containing non woven fibrous polyethylene terephthalate, the first scaffold being positioned within the chamber between the upper channel and the middle channel, and the second scaffold being positioned within the chamber between the middle channel and the lower channel.

58 Claims, 2 Drawing Sheets

BIOREACTOR FOR CELL CULTURE

RELATED APPLICATION

This application is a continuation-in-part and claims priority from application Ser. No. 10/645,350 which was filed on Aug. 21, 2003, now U.S. Pat. No. 6,875,605 and which claimed priority from application Ser. Nos. 60/405,040 and 60/405,041, both filed on Aug. 21, 2002; in addition this application claims priority to co-pending provisional application Ser. No. 60/494,907, which was filed on Aug. 13, 2003; all priority applications are incorporated herein by reference in their entirety.

FIELD OF THE INVENTION

The present invention relates to the field of cell culture and, more particularly, to a perfusion bioreactor apparatus having multiple layers of matrices for growing cells therein and to its associated methods.

BACKGROUND OF THE INVENTION

Biochemical engineering is a professional discipline which deals in the development, design, operation, control, and analysis of biological and biochemical processes. While the discipline as been practiced in one form or another since ancient times, particularly in the production of fermentation products such as alcoholic beverages, modern biochemical engineering began in the 1940s with the large scale production of penicillin. Goods manufactured by biochemical engineering processes include health care products such as antibiotics, vaccines, foods and beverages. Additionally, chemicals and fuels are also biochemically engineered, for example, organic acids, solvents, enzymes and alcohols.

More recently, biochemical engineering techniques have been applied to the culture of human and animal tissue cells, which requires the design, operation and control of bioreactors generally intended to optimize the growth of the cultured cells. Many mammalian and microbial cell cultures are subject to formation of cell aggregates resulting in intraparticle diffusion resistance which must be accounted for in bioreactor parameters. Moreover, the scale-up of laboratory prototype bioreactors is usually dependent on the specific design of the bioreactor.

SUMMARY OF THE INVENTION

With the foregoing in mind, the present invention advantageously provides a bioreactor for cell culture. The present bioreactor comprises a chamber and first and second cell support scaffolds. The chamber has three channels therethrough for conducting fluids, the three channels including an upper channel, a middle channel, and a lower channel, each the channel having an inlet and an outlet approximately opposite along the channel from the inlet. The first and second cell support scaffolds, each comprises at least one three-dimensional porous matrix containing non woven fibrous polyethylene terephthalate, the first scaffold being positioned within the chamber between the upper channel and the middle channel, and the second scaffold being positioned within the chamber between the middle channel and the lower channel.

In another embodiment, the invention provides an apparatus for cell culture. The apparatus includes a plurality of bioreactors, each individual bioreactor including a chamber having three channels therethrough for containing fluids, the three channels including an upper channel, a middle channel, and a lower channel, each the channel having an inlet and an outlet approximately opposite along the channel from the inlet, and a plurality of cell support scaffolds comprising at least first and second cell support scaffolds, each the scaffold comprising a three-dimensional porous matrix containing non woven fibrous polyethylene terephthalate, the first scaffold positioned within the chamber between the upper channel and the middle channel, and the second scaffold positioned within the chamber between the middle channel and the lower channel. Additionally, the apparatus also includes a reservoir for a fluid medium, a plurality of conduits fluidly connected between the at least one reservoir and the three channels, a pump fluidly connected through the plurality of conduits between the reservoir and the three channels to pump a flow of fluid medium therethrough, and a plurality of valves positioned to control the flow of fluid medium through each individual bioreactor of the plurality of bioreactors.

Accordingly, the present perfusion bioreactor includes multiple layers of matrices for cells to grow in. The preferred matrix material is three-dimensional, having a porous consistency to allow for flow of fluids therethrough and for cells to penetrate the matrix and establish themselves therein. Fluid channels in the bioreactor may carry a fluid medium which may liquid or may be an aqueous gel.

A preferred medium for use in the apparatus may include growth factors and signaling molecules which function to induce specific cell functions, or to direct cell movement by influencing their penetration into the matrix, either positively or negatively. These growth factors and/or signaling molecules may be immobilized in a gel contained in a conduit within the bioreactor. Moreover, magnetic particles (MP) may be introduced in the bioreactor, for example, magnetically responsive particles tagged with specific antibodies (AB) directed to certain cell types in the bioreactor to serve as a means of labeling and/or sorting the cells. Cells tagged with these MPAB may be removed from the bioreactor by the application of an external magnetic field, or they may be drawn to concentrate in a predetermined area within the bioreactor.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims. Accordingly, FIGS. 1 and 2 illustrate the presently described bioreactor for cell culture.

Those skilled in the art will recognize that the present invention describes a bioreactor 10 for cell culture, that is, a device through which an inoculum containing cells is filtered so that the cells will pass into and substantially adhere to a three-dimensional porous matrix 12 which serves both as the filter and as the support substrate upon which the cells grow, a support "scaffold", if you will. The bioreactor also includes channels 14 through which the inoculum may be introduced, and through which fluid media may be introduced for cell nourishment and maintenance. The present bioreactor is particularly useful for recovering and culturing predetermined cells from an inoculum containing human bone marrow.

Figure 1:
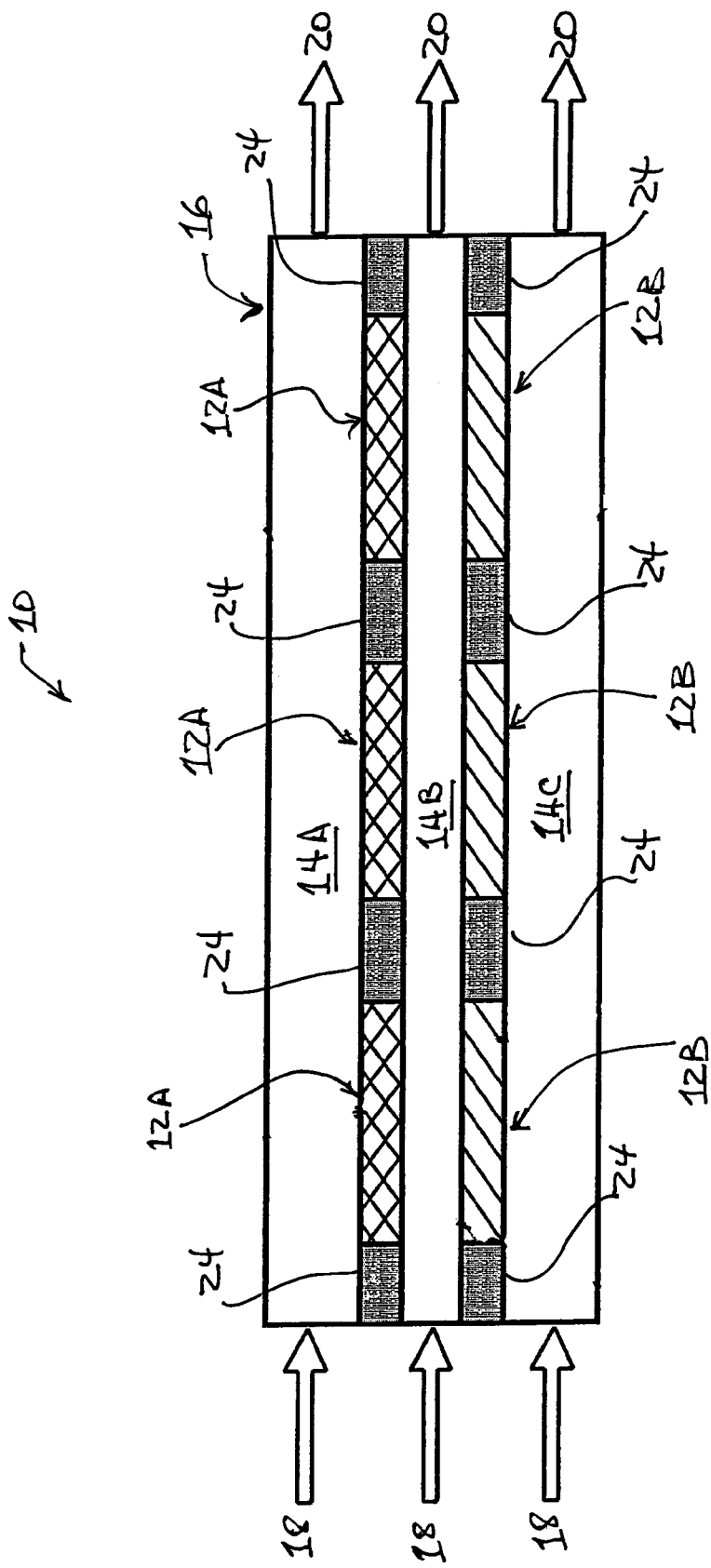
FIG. 1 illustrates a bioreactor according to an embodiment of the present invention.
Figure 2:
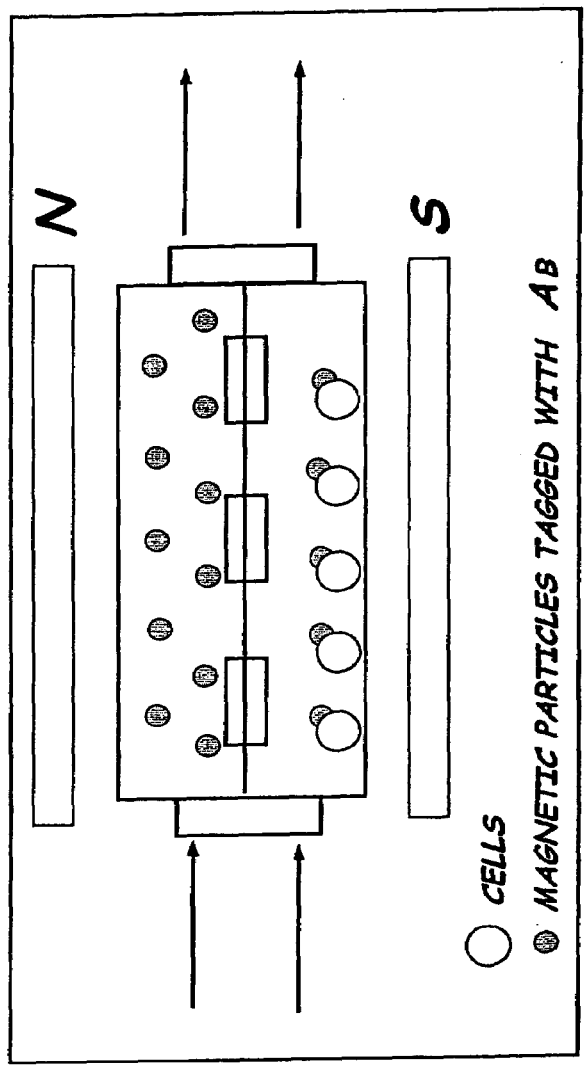
FIG. 2 shows a pattern of secondary channels formed in the bioreactor matrix (A), and cells influenced by antibody-tagged magnetic particles affected by an applied magnetic field (B).
Figure 2:
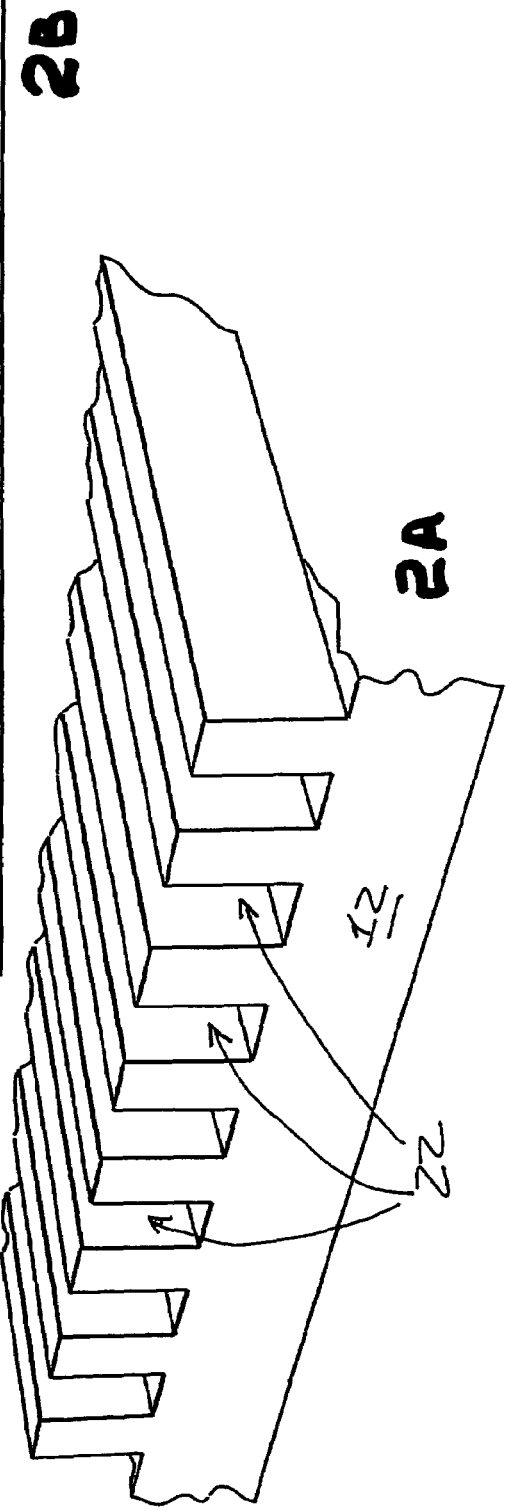

A preferred embodiment of the present bioreactor is shown in FIG. 1 and comprises a chamber 16, and first 12A and second 12B cell support scaffolds. The chamber 16, which is the bioreactor container, has three channels therethrough for conducting fluids, the three channels including an upper channel 14A, a middle channel 14B, and a lower channel 14C, each the channel having an inlet 18 and an outlet 20 approximately opposite along the channel from the inlet. The first 12A and second 12B cell support scaffolds each comprise at least one three-dimensional porous matrix containing non woven fibrous polyethylene terephthalate, the first scaffold being positioned within the chamber 16 between the upper channel 14A and the middle channel 14B, and the second scaffold being positioned within the chamber between the middle channel and the lower channel 14C.

Various other features of the above described preferred embodiment include a bioreactor 10 wherein the first 12A and second 12B scaffolds are approximately equal in thickness, and a bioreactor wherein the first and second scaffolds are unequal in thickness from each other. Moreover, the first 12A and second 12B scaffolds may be of approximately equal porosity, or may be unequal in porosity. These differences may be of importance, depending on the type of cell being deposited and cultured in the particular matrix. Furthermore, in order to influence movement of seeded cells into the matrices 12 of the bioreactor 10, at least one of the three channels 14 may contain a fluid having one or more cell growth factors, or other cell attractants or repellents.

In another embodiment, the present bioreactor 10 may include first 12A and second 12B scaffolds further comprising one or more secondary channels 22 formed in the porous matrix. For example, the first 12A and second 12B scaffolds may further comprise one or more secondary channels 22 formed on a surface of the porous matrix, as illustrated in FIG. 2.

The bioreactor 10 above described may also include an embodiment wherein at least one of the three channels 14 contains a fluid having one or more factors effective for influencing cell migration through the scaffolds 12. In this manner specific cells may be selected from a mixed population of cells and attracted into the porous matrix for attachment and growth. Advantageously, at least one of the three channels 14 may contain a cell nourishing medium. The skilled will recognize that the fluid media mentioned may be in the form of a gel medium, which may be contained in at least one of the three channels 14.

The bioreactor 10 preferably has a chamber 16 which is elongated, having the three channels 14 extending through a lengthwise extent of the chamber, having each channel's inlet 18 positioned at a first lateral periphery of the elongated chamber, and having each the channel's outlet 20 positioned at a second lateral periphery of the elongated chamber and generally opposite the first lateral periphery. More specifically, the chamber 16 may comprise a cylinder, having the three channels 14 extending through a lengthwise extent of the cylinder, of which FIG. 1 could be a cross section. The bioreactor 10 also includes an embodiment wherein the chamber 16 further comprises a valve (not shown) positioned to control each the inlet 18. Moreover, the chamber 16 may further comprise a valve (not shown) positioned to control each the outlet 20. Yet additionally, the first 12A and second 12B scaffold may comprise a plurality of individual scaffold members separated from each other by non-scaffold material 24, as shown in FIG. 1.

In use, the bioreactor 10 embodiment described above includes a chamber 16 wherein the middle channel 14B contains a fluid carrying a plurality of cell types, wherein the upper channel 14A contains a fluid having one or more factors effective for influencing migration of at least a first cell type from the middle channel into the first scaffold 12A, and wherein the lower channel 14C contains a fluid having one or more factors effective for influencing migration of at least a second cell type from the middle channel into the second scaffold 12B. It is understood that at least one of the three channels 14 contains an inoculum comprising cells. The invention is particularly useful when used so that at least one of the three channels 14 contains an inoculum comprising bone marrow and, more specifically, an inoculum comprising human bone marrow for recovery of and culture of specific cells from the bone marrow.

The skilled will understand that the number of channels 14 and scaffolds 12 may be increased beyond the first described bioreactor having three channels and two scaffolds. Accordingly, a further embodiment of the present invention includes a bioreactor 10 comprising a chamber 16 having a plurality of channels 14 therethrough for conducting fluids, each individual channel having an inlet 18 and an outlet 20, and a plurality of cell support scaffolds 12, each scaffold of the plurality comprising at least one three-dimensional porous matrix containing non woven fibrous polyethylene terephthalate, and wherein each scaffold of the plurality is positioned within the chamber 16 between two individual channels of the plurality of channels.

The invention also includes an apparatus for cell culture in which a plurality of the bioreactors 10 described above are connected together to increase cell culture productivity. In this embodiment, an apparatus for cell culture comprises a plurality of bioreactors 10, each individual bioreactor including a chamber 16 having three channels 14 therethrough for containing fluids, the three channels including an upper channel 14A, a middle channel 14B, and a lower channel 14C, each the channel having an inlet 18 and an outlet 20 approximately opposite along the channel from the inlet, and a plurality of cell support scaffolds 12 comprising at least first 12A and second 12B cell support scaffolds, each the scaffold comprising a three-dimensional porous matrix containing non woven fibrous polyethylene terephthalate, the first scaffold positioned within the chamber between the upper channel and the middle channel, and the second scaffold positioned within the chamber between the middle channel and the lower channel. A reservoir (not shown) for a fluid medium is connected in the apparatus by a plurality of conduits fluidly connected between the reservoir and the three channels 14. A pump (not shown) is fluidly connected through the plurality of conduits between the reservoir and the three channels 14 to pump a flow of fluid medium therethrough, and a plurality of valves (not shown) are positioned to control the flow of fluid medium through each individual bioreactor 10 of the plurality of bioreactors. The skilled will recognize that through the use of a sufficient number of valves, the flow rate of fluid through of each channel may be controlled appropriately for cell seeding, for cell growth and culture, and for cell removal from the bioreactor.

As described above, preferred embodiments of the invention are shown in FIGS. 1 and 2. The present perfusion bioreactor 10 includes multiple layers of matrices 12 for cells to grow in. The matrix material, preferably consisting essentially of polyethylene terephthalate, is three-dimensional, having a random porous consistency to allow for flow of fluids therethrough and for cells to penetrate the matrix 12 and establish themselves therein. Fluid channels 14 in the bioreactor chamber 16 carry cell support medium which may liquid or aqueous gels. The medium may include growth factors and signaling molecules which function to induce specific cell functions, or to direct cell movement. These growth factors and/or signaling molecules may be immobilized in a gel contained in a conduit within the bioreactor 10.

In a variation of the present bioreactor invention, as shown in FIG. 2B, magnetically responsive particles may be introduced in the bioreactor, for example, tagged with specific antibodies directed to certain cell types to serve as a means of labeling and/or sorting the cells. For example, cells tagged with magnetic particles may be urged to exit the bioreactor by the application of an external magnetic field, or may be drawn to concentrate in a predetermined area within the bioreactor chamber.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A bioreactor for cell culture, said bioreactor comprising:
    a chamber having three channels therethrough for conducting fluids, said three channels including an upper channel, a middle channel, and a lower channel, each said channel having an inlet and an outlet approximately opposite along said channel from said inlet; and
    first and second cell support scaffolds, each scaffold comprising at least one three-dimensional porous matrix containing non woven fibrous polyethylene terephthalate, said first scaffold being positioned within said chamber between said upper channel and said middle channel, and said second scaffold being positioned within said chamber between said middle channel and said lower channel.

2. The bioreactor of claim 1, wherein said first and second scaffolds are approximately equal in thickness.

3. The bioreactor of claim 1, wherein said first and second scaffolds are unequal in thickness from each other.

4. The bioreactor of claim 1, wherein said first and second scaffolds are of approximately equal porosity.

5. The bioreactor of claim 1, wherein said first and second scaffolds are unequal in porosity.

6. The bioreactor of claim 1, wherein at least one of said three channels contains a fluid having one or more cell growth factors.

7. The bioreactor of claim 1, wherein at least one of said first and second scaffolds further comprises one or more secondary channels formed in said porous matrix.

8. The bioreactor of claim 1, wherein at least one of said first and second scaffolds further comprises one or more secondary channels formed on a surface of said porous matrix.

9. The bioreactor of claim 1, wherein at least one of said three channels contains a fluid having one or more factors effective for influencing cell migration through said scaffolds.

10. The bioreactor of claim 1, wherein at least one of said three channels contains a cell nourishing medium.

11. The bioreactor of claim 1, wherein at least one of said three channels contains a gel medium.

12. The bioreactor of claim 1, wherein said middle channel contains a gel medium.

13. The bioreactor of claim 1, wherein said chamber is elongated, having said three channels extending through a lengthwise extent of said chamber, having each channel's inlet positioned at a first lateral periphery of said elongated chamber, and having each said channel's outlet positioned at a second lateral periphery of said elongated chamber and generally opposite said first lateral periphery.

14. The bioreactor of claim 1, wherein said chamber comprises a cylinder, having said three channels extending through a lengthwise extent of said cylinder.

15. The bioreactor of claim 1, wherein said chamber further comprises a valve positioned to control each said inlet.

16. The bioreactor of claim 1, wherein said chamber further comprises a valve positioned to control each said outlet.

17. The bioreactor of claim 1, wherein each said first and second scaffold comprises a plurality of individual scaffold members separated from each other by non-scaffold material.

18. The bioreactor of claim 1, wherein said middle channel contains a fluid carrying a plurality of cell types, wherein said upper channel contains a fluid having one or more factors effective for influencing migration of at least a first cell type from said middle channel into said first scaffold, and wherein said lower channel contains a fluid having one or more factors effective for influencing migration of at least a second cell type from said middle channel into said second scaffold.

19. The bioreactor of claim 1, wherein at least one of said three channels contains an inoculum comprising cells.

20. The bioreactor of claim 1, wherein at least one of said three channels contains an inoculum comprising bone marrow.

21. The bioreactor of claim 1, wherein at least one of said three channels contains an inoculum comprising human bone marrow.

22. A bioreactor for cell culture, said bioreactor comprising:
- a chamber having a plurality of channels therethrough for conducting fluids, each individual channel having an inlet and an outlet; and
- a plurality of cell support scaffolds, each scaffold of the plurality comprising at least one three-dimensional porous matrix containing non woven fibrous polyethylene terephthalate, and wherein each scaffold of the plurality is positioned within said chamber between two individual channels of said plurality of channels.

23. The bioreactor of claim 22, wherein said plurality of cell support scaffolds includes individual scaffolds approximately equal in thickness.

24. The bioreactor of claim 22, wherein said plurality of cell support scaffolds includes individual scaffolds unequal in thickness from each other.

25. The bioreactor of claim 22, wherein said plurality of cell support scaffolds includes individual scaffolds of approximately equal porosity.

26. The bioreactor of claim 22, wherein said plurality of cell support scaffolds includes individual scaffolds unequal in porosity.

27. The bioreactor of claim 22, wherein at least one scaffold of said plurality of cell support scaffolds further comprises one or more secondary channels formed in said porous matrix.

28. The bioreactor of claim 22, wherein at least one scaffold of said plurality of cell support scaffolds further comprises one or more secondary channels formed on a surface of said porous matrix.

29. The bioreactor of claim 22, wherein one or more channels of said plurality of channels contains a fluid having one or more cell growth factors.

30. The bioreactor of claim 22, wherein one or more channels of said plurality of channels contains a fluid having one or more factors effective for influencing cell migration through said scaffolds.

31. The bioreactor of claim 22, wherein one or more channels of said plurality of channels contains a cell nourishing medium.

32. The bioreactor of claim 22, wherein one or more channels of said plurality of channels contains a gel medium.

33. The bioreactor of claim 22, wherein one or more individual chambers of said plurality of chambers comprises a valve positioned to control at least one inlet.

34. The bioreactor of claim 22, wherein one or more individual chambers of said plurality of chambers comprises a valve positioned to control each said outlet.

35. The bioreactor of claim 22, wherein one or more individual scaffold of said plurality of scaffolds comprises a plurality of individual scaffold members separated from each other by non-scaffold material.

36. The bioreactor of claim 22, wherein at least one channel of said plurality of channels contains a fluid carrying a plurality of cell types, and wherein at least an adjacent channel contains a fluid having one or more factors effective for influencing migration of at least one cell type from said plurality of cell types into a scaffold positioned between said channels.

37. The bioreactor of claim 22, wherein at least one channel of said plurality of channels contains an inoculum comprising cells.

38. The bioreactor of claim 22, wherein at least one channel of said plurality of channels contains an inoculum comprising bone marrow.

39. The bioreactor of claim 22, wherein at least one channel of said plurality of channels contains an inoculum comprising human bone marrow.

40. An apparatus for cell culture, comprising:
- a plurality of bioreactors, each individual bioreactor including a chamber having three channels therethrough for containing fluids, said three channels including an upper channel, a middle channel, and a lower channel, each said channel having an inlet and an outlet approximately opposite along said channel from said inlet, and a plurality of cell support scaffolds comprising at least first and second cell support scaffolds, each said scaffold comprising a three-dimensional porous matrix containing non woven fibrous polyethylene terephthalate, said first scaffold positioned within said chamber between said upper channel and said middle channel, and said second scaffold positioned within said chamber between said middle channel and said lower channel;
- a reservoir for a fluid medium;
- a plurality of conduits fluidly connected between said at least one reservoir and said three channels;
- a pump fluidly connected through said plurality of conduits between said reservoir and said three channels to pump a flow of fluid medium therethrough; and
- a plurality of valves positioned to control the flow of fluid medium through each individual bioreactor of the plurality of bioreactors.

41. The apparatus of claim 40, wherein said first and second scaffolds are approximately equal in thickness.

42. The apparatus of claim 40, wherein said first and second scaffolds are unequal in thickness from each other.

43. The apparatus of claim 40, wherein said first and second scaffolds are of approximately equal porosity.

44. The apparatus of claim 40, wherein said first and second scaffolds are unequal in porosity.

45. The apparatus of claim 40, wherein at least one scaffold of said plurality of cell support scaffolds further comprises one or more secondary channels formed in said porous matrix.

46. The apparatus of claim 40, wherein at least one scaffold of said plurality of cell support scaffolds further comprises one or more secondary channels formed on a surface of said porous matrix.

47. The apparatus of claim 40, wherein at least one of said three channels contains a fluid having one or more cell growth factors.

48. The apparatus of claim 40, wherein at least one of said three channels contains a fluid having one or more factors effective for influencing cell migration through said scaffolds.

49. The apparatus of claim 40, wherein at least one of said three channels contains a cell nourishing medium.

50. The apparatus of claim 40, wherein at least one of said three channels contains a gel medium.

51. The apparatus of claim 40, wherein said middle channel contains a gel medium.

52. The apparatus of claim 40, wherein said chamber is elongated, having said three channels extending through a lengthwise extent of said chamber, having each channel's inlet positioned at a first lateral periphery of said elongated chamber, and having each said channel's outlet positioned at a second lateral periphery of said elongated chamber and generally opposite said first lateral periphery.

53. The apparatus of claim 40, wherein said chamber comprises a cylinder, having said three channels extending through a lengthwise extent of said cylinder.

54. The apparatus of claim 40, wherein said chamber further comprises a valve positioned to control each said inlet.

55. The apparatus of claim 40, wherein said chamber further comprises a valve positioned to control each said outlet.

56. The apparatus of claim 40, wherein each said first and second scaffold comprises a plurality of individual scaffold members separated from each other by non-scaffold material.

57. The apparatus of claim 40, wherein said plurality of bioreactors comprises at least four bioreactors.

58. The apparatus of claim 40, wherein in at least one bioreactor of said plurality of bioreactors said middle channel contains a fluid carrying a plurality of cell types, wherein said upper channel contains a fluid having one or more factors effective for influencing migration of at least a first cell type from said middle channel into said first scaffold, and wherein said lower channel contains a fluid having one or more factors effective for influencing migration of at least a second cell type from said middle channel into said second scaffold.

* * * * *

UNITED STATES PATENT AND TRADEMARK OFFICE
CERTIFICATE OF CORRECTION

| | | |
|---|---|---|
| PATENT NO. | : 6,943,008 B1 | Page 1 of 1 |
| APPLICATION NO. | : 10/918657 | |
| DATED | : September 13, 2005 | |
| INVENTOR(S) | : Teng Ma | |

It is certified that error appears in the above-identified patent and that said Letters Patent is hereby corrected as shown below:

Column 1, Line 14

Insert: -- STATEMENT OF GOVERNMENT INTEREST

This invention was made with government support under DAMD17-02-1-0704 awarded by the United States Army Medical Research and Material Command. The government has certain rights in the invention. --

Signed and Sealed this
Fifteenth Day of May, 2012

David J. Kappos
*Director of the United States Patent and Trademark Office*